United States Patent [19]

Schultz et al.

[11] Patent Number: 5,188,639
[45] Date of Patent: Feb. 23, 1993

[54] PRODUCT FOR IMPROVED PERMANENT WAVING OF HAIR AND SIMULTANEOUSLY COLORING AND PERMANENTLY WAVING HAIR AND METHOD THEREFOR

[75] Inventors: Thomas M. Schultz, Ridgefield, Conn.; Jitendra Patel, Coon Rapids, Minn.; Stephanie Wong, Bridgeport, Conn.

[73] Assignee: Shiseido Co., Ltd., Tokyo, Japan

[21] Appl. No.: 847,788

[22] Filed: Mar. 6, 1992

Related U.S. Application Data

[62] Division of Ser. No. 612,227, Nov. 13, 1990, Pat. No. 5,094,662.

[51] Int. Cl.$^5$ ................................................ A61K 7/13
[52] U.S. Cl. ................................................ 8/405; 8/406; 8/407; 8/409; 8/432; 132/201; 132/208; 252/301.16; 424/70
[58] Field of Search .................. 8/405, 406, 407, 409, 8/432; 252/301.16; 132/201, 208; 424/70

[56] References Cited

U.S. PATENT DOCUMENTS

| | | | |
|---|---|---|---|
| 3,989,447 | 11/1976 | Kolopissis et al. | 8/407 |
| 4,027,008 | 5/1977 | Sokol | 8/432 |
| 4,048,338 | 9/1977 | Gerecht | 8/405 |
| 4,781,724 | 11/1988 | Wajaroff et al. | 8/432 |
| 4,787,911 | 11/1988 | Sebag et al. | 8/405 |
| 4,932,977 | 6/1990 | Schultz | 8/423 |

FOREIGN PATENT DOCUMENTS 2-076807 3/1990 Japan.

Primary Examiner—A. Lionel Clingman
Assistant Examiner—William S. Parks
Attorney, Agent, or Firm—Melvin I. Stoltz

[57] ABSTRACT

By combining a fluoroscein-based dye with a mercaptan based permanent waving composition and maintaining the pH of the resulting composition between about 2.5 and 4.5, a composition is achieved which simultaneously colors and permanently waves the hair. In addition, even if no coloring or dying of the hair is desired, the use of a colorless or complimentary fluoroscein-based dye with the mercaptan based permanent waving composition achieves a composition which imparts a substantially improved curl configuration to the hair as well as substantially longer lasting curls. Preferably, the mercaptan based permanent waving composition employed comprises an ester of either thioglycolic acid, thiolactic acid, or the amide of 2-aminoethanethiol.

5 Claims, No Drawings

PRODUCT FOR IMPROVED PERMANENT WAVING OF HAIR AND SIMULTANEOUSLY COLORING AND PERMANENTLY WAVING HAIR AND METHOD THEREFOR

This application is a division of application Ser. No.07/612,227, Nov. 13, 1990, now U.S. Pat. No. 5,094,662.

TECHNICAL FIELD

This invention relates to products for permanently waving hair and, more particularly, to products for permanently waving hair with substantially improved curl retention and, if desired simultaneously coloring the hair.

BACKGROUND ART

In view of the unique composition of hair fibers and the numerous changes that occur in styles and fashion, both the waving of hair and the dyeing of hair have long been of particular interest. In particular, hair color alteration by dyeing while permanent waving hair for long-lasting style retention have long been sought by many individuals. However, due to the composition of hair fiber, either the color or curls are not retained as long as desired and the simultaneous permanent waving and dyeing of hair fibers has not yet been achieved by any commercially available product.

In order to best understand the reasons for the inability of the hair fiber to retain curls for substantially long time periods or to be simultaneously permanently waved and colored, it is important to understand that hair is composed of a unique protein material called "keratin" and which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S-S) to give keratin protein (K-S-S-K). Only by chemical action can this covalent linkage be broken.

In this regard, many prior art compositions have been developed for the "cold permanent waving" of hair. Typically, these prior art systems treat the hair with a reducing agent which breaks the disulfide (cystine) linkage in the hair. This chemical process typically follows that after the hair is wound around a curling rod.

In general, permanent hair waving is usually carried out by subjecting the hair to reagents containing a free—thiol group e.g.,—SH. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations:

$$KSSK + 2RSH \rightleftharpoons 2KSH + RSSR$$

$$KSSK + RSH \rightleftharpoons KSSR + KSH$$

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction products formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, typically hydrogen peroxide, and can be illustrated by the following chemical reaction:

$$2 KSH + H_2O_2 \rightarrow KSSK + 2H_2O$$

In the art of permanent waving, there is much trial and error, with the hair being over-processed, in some instances. The characteristics of over-processing are raspy feel to the hair or a bleaching of the natural underlying color. Structural evaluation of the hair fiber by physical and chemical analyses usually reveals that the structural integrity of the hair is lessened, which is evidenced by either an increase in the amount of cysteine and cystic acid; a lessening of the cystine content relative to the hair not so processed; or loss of tensile properties.

Some detrimental effect to hair fiber is unavoidable, as the process of permanent waving involves controlled bond scission of the disulfide linkages within the keratin proteins. The recovery of these disulfides is the determining factor for the tightness of the curls and overall tensile strength.

One problem typically encountered with the use of mercaptan reducing agents for the permanent waving of hair is that one lotion strength is needed for virgin hair, while a different lotion strength is needed for damaged or hair that had been previously chemically processed and, hence, difficult to wave. This problem is further compounded when there is a mixture of both damaged as well as normal hair fibers on a head of hair to be permanently waved. In particular, with either oxidatively or deposit colored dyed hair, the subsequent application of mercaptan reducing agents causes a discoloring of the imparted dye in the hair fiber, thereby leaving the hair with an undesired or different shade than had previously existed before the process.

Another problem typically found in the prior art occurs when an individual wishes to dye hair which had been permanently waved. In these circumstances, the dye uptake will usually be uneven from the root to the tip of the hair fibers due to the structural alteration caused to the hair fiber by the permanent wave process.

In practice, this problem is often circumvented by waiting for the hair to "heal", by allowing for a substantial time interval in which aerial oxidation reseals the excessively damaged areas, thereby providing hair fibers which are more amenable to dye uptake in a level manner.

Although the consumer has long sought to have a composition and process which would enable both color and permanent waving to be achieved simultaneously, no prior art system has been able to provide an effective or reliable composition which would enable simultaneous dyeing and permanent waving of hair fibers. In fact, even though this need has existed in the art for decades, no successful commercial product has been attained which satisfies the consumers' need.

One of the difficulties encountered in providing a prior art composition which will achieve this simultaneous dyeing and permanent waving of hair fibers is due to the chemical nature of typical prior art dyestuffs. In general, oxidative dyestuffs are irreversibly altered in their color upon contacting sulfurous materials, such as found in the permanent wave compositions. Consequently, oxidative dyestuffs cannot be successfully employed with permanent waving compositions.

Alternatively, semi-permanent dyestuffs may be employed and have been used to provide a temporary dyeing of the hair. However, such dyestuffs tend to be removed from the hair upon washing and rubbing, or by the increased porosity of hair resulting from chemical processing. Consequently, their incorporation into a permanent waving process does not provide the desired consumer result, since they are incapable of providing the permanent hair coloring effect desired by the consumer.

A further problem found with oxidatives or direct dyes is the fact that these materials are typically irritants or sensitizers of human skin. Consequently, these dyes should be employed either by skilled technicians or home users who are extremely careful to apply the dyes explicitly in accordance with included directions.

Although numerous attempts have been made in the prior art to provide a combined permanent waving and hair dye product, no prior art product has been successful in achieving a universally applicable or a commercially acceptable product.

Representative prior art attempts to meet the commercial demand are found in various prior art patents. Those patent includes U.S. Pat. No. 4,630,621, wherein a common oxidative dyestuff is added to the neutralizing composition for subsequent application to the hair after the hair has been treated with a permanent wave reducing solution. However, as discussed above, such oxidated dyestuffs must be used carefully by skilled technicians or individuals who are extremely cautious and careful with the dyes, due to the irritation that may result on the skin of the user.

In U.S. Pat. No. 4,781,724, a process is disclosed for simultaneously dyeing and permanently waving white and gray hair. Although this patent teaches the incorporation of specific dyestuffs in the permanent wave reducing solution, the dyes taught herein are specifically limited to use on white and gray hair only. In addition, as will be detailed below, the operative pH range of the composition incorporating the dyestuffs is substantially greater than the operative pH range of the present invention.

Other prior art patents, such as U.S. Pat. No. 3,299,682, U.K. Patent No. 1,077,758 and U.S. Pat. No. 4,844,712 teach the use of various dyestuffs. However, these patents do not provide any teaching of combining the dye with a permanent wave composition for achieving simultaneous hair dyeing and permanent waving.

Furthermore, these prior art patents do not, in any way, teach or suggest a permanent waving composition which comprises a pH ranging between 3.0 and 4.5. In fact, any of those prior art references which discuss permanent waving specifically teach away from employing a permanent wave at this particular pH range and, instead, teach compositions wherein the pH is 6.0 or greater.

Therefore, it is a principal object of the present invention to provide a permanent waving composition which is capable of providing substantially tighter curls and longer lasting curls than previously attained in prior art systems.

Another object of the present invention is to provide a permanent waving composition having the characteristic features described above which is also capable of simultaneously dyeing the hair as an integral part of the permanent waving process, when desired by the consumer.

Another object of the present invention is to provide a permanent waving composition and process for application thereof having the characteristic features described above which is capable of providing optimum results at a pH level previously found unsuitable for permanent waving of hair.

Other and more specific objects will in part be obvious and will in part appear hereinafter.

DISCLOSURE OF THE INVENTION

By employing the present invention, prior art difficulties and drawbacks have been eliminated and tighter, more durable permanent waving results are achieved as well as the ability to simultaneously color and permanently wave the hair. It has been found that the prior art inabilities are completely eliminated by incorporating fluoroscein based dyestuffs in a permanent wave composition comprising a mercaptan selected from the group consisting of an ester of either thioglycolic acid, thiolactic acid, or the amide of 2-aminoethanethiol. Furthermore, the resulting composition is maintained at a pH of between about 2.5 and 4.5.

Depending upon the fluoroscein based dyestuff employed, the hair can be simultaneously permanently waved, while also being dyed. If the actual dyeing of the hair is not desired, the fluoroscein based dyestuff can either be colorless or may employ a complimentary color, which would highlight the hair.

Regardless of whether actual coloring is imparted to the hair fibers, it has been found that the combination of a fluoroscein based dyestuff with the particular permanent waved composition, when maintained at a pH of between about 2.5 and 4.5, provides heretofore unattainable results. In particular, the hair is permanently waved with substantially improved curl configuration, while also providing curls which are retained for substantially longer time periods than ever previously achieved.

By employing the present invention, it has been found that the hair is permanently waved in a tight curl and, when desired, is also colored in a level, uniform and controlled fashion. It is believed that the fluoroscein based dyestuff acts synergistically in combination with the permanent wave solution to promote curl impartation, resulting in substantially improved results than ever previously attained. Furthermore, the permanent wave composition of this invention operates at a pH of between about 2.5 and 4.5, a pH range which has typically been incapable of providing acceptable results.

In developing the present invention, it has been found that the fluoroscein based dyestuff should comprise only dyestuffs which have been approved by the Food and Drug Administration. Consequently, all of the dyestuffs employed in the present invention comprise either F,D and C colors (suitable for foods, drugs, and cosmetics) or D and C colors (suitable for drugs and cosmetics). In addition to employing a fluoroscein based dye, it is also required that the permanent wave composition comprise an ester of either thioglycolic acid, thiolactic acid, or the amide of 2-aminoethanethiol. It has been found that only these mercaptans in combination with a fluoroscein based dyestuff provides the synergistic interaction herein described.

It has also been discovered that all of the suitable mercaptans in accordance with this invention cause the fluoroscein based dyestuff to become discolored or colorless when intermixed therewith. In fact, this phenomenon has been found to represent a characteristic requisite for a composition that is capable of concurrently permanently waving and coloring the hair.

In the preferred composition, the mercaptan comprises an ester of thioglycolic acid with the ester being derived from one selected from the group consisting of glycerin, glyercol and glycosyl. In addition, it has been found that the concentration of the fluoroscein based dyestuff should range between 0.0000001 and 8.0% by weight of the total composition, while the ester of the thioqlycolic acid preferably comprises a concentration ranging between 0.0001 and 30% by weight of the total composition.

The invention accordingly comprises a composition possessing the features, proportions, and the relation of constituents, as well as the several steps and the relation of one or more of such steps with respect to each of the other, all as fully detailed herein, with the scope of the invention being indicated in the claims.

BEST MODE FOR CARRYING OUT THE INVENTION

In order to demonstrate the unique capabilities of the present invention, the following examples are provided, detailing various aspects of this invention. These examples are intended as a teaching of the best mode for carrying out the present invention and are not intended to limit, in any manner, the breadth of this discovery.

By employing the compositions of this invention, substantially improved curl retention and hair strength are attained. In order to show the substantial enhancements provided by the present invention, a plurality of comparative tests were conducted on hair permanently waved with the different compositions formulated in accordance with the present invention. The results attained were compared to standard permanent wave compositions, in order to demonstrate the efficacy of the present invention.

In order to provide a useful and instructive comparative analysis, various test mixtures were prepared and applied to the hair as detailed below. In Table I, the permanent wave composition employed in the test mixtures are detailed, while Table II provides the compositions employed for the fluoroscein-based dyes.

TABLE I

| Permanent Wave Compositions | | |
|---|---|---|
| Part A | Glycerine monothioglycolate 70% in glycerine | 32.5% |
| Part B | De-ionized water | 98.44% |
| | Ammonium Chloride | 1.50% |
| | Preservative | 0.06% |
| Part C | Glycerin-thiolactic acid ester (in 25% - glycerin) | 32.5% |
| Part D | De-ionized water | 88.5% |
| | Ammonium chloride | 1.5% |
| | Animal protein, cocohydrolyzed potassium salt | 1.0% |

TABLE I-continued

| Permanent Wave Compositions | |
|---|---|
| Laureth ether | 2.0% |
| Fragrance | 1.0% |
| Polystyrene emulsifier | 2.0% |
| Ammonium hydroxide (28%) solution | 4.0% |

TABLE II

| Part E | Propylene glycol | 76.8% |
|---|---|---|
| | F, D&C Red #21 | 20.0% |
| | Monoethanolamine | 3.2% |
| Part F | De-ionized water | 79.8% |
| | F, D&C Red #22 | 20.0% |
| | Preservative | 0.2% |
| Part G | De-ionized water | 94.8% |
| | F, D&C Red #28 | 5.0% |
| | Preservative | 0.2% |
| Part H | De-ionized water | 79.8% |
| | F, D&C Blue #1 | 20.0% |
| | Preservative | 0.2% |

In Table III, each of the compositions tested is clearly presented as a separate example, with the test results attained for each test sample also provided for ease of comparison. In each of the examples provided in Table III, about one gram of medium brown hair was crimped at its end with a metal staple and wetted with water. Next, the hair was wrapped about a styling rod, secured with a rubber band and then saturated with the particular composition mixture detailed in Table III.

The particular mixture was allowed to remain on the hair for about twenty minutes under a plastic wrapper, while being warmed with hot water. At the end of the required time period, the hair was rinsed with running tap water and then saturated with a solution of 2% hydrogen peroxide stabilized with 0.2% phosphoric acid. This composition remained on the hair for about five minutes and then the hair was thoroughly rinsed with tap water.

The test results provided in Table III provide the degree of curl found for each test sample when the hair was dryed as well as after forty-eight hour exposure to 90% humidity. For the purpose of this comparative study, the results provided represent the degree of curl (C), which is defined by the following equation:

$$C = \frac{H - d}{n}$$

where H is the total hair length d is the distance from the hair root to the first curl, and n is the total number of curls.

In addition to comparing the curl resiliency for each of the test samples, the strength of the resulting hair fibers was also determined for most of the test samples. These results are also provided in Table III and were determined by using a tensile property determining apparatus such as is available from the Instron Corporation, specifically their Model 20/20 Machine.

The results provided in Table III represent the amount of change in tensile strength of the hair fiber as a comparison before and after the treatment of the hair. In order to determine the tensile strength of the resulting hair fiber, the force needed to elongate the hair fiber by 10% before treatment is determined as well as the force needed to elongated the hair fiber by 10% after treatment. The test results provided in Table III represent the pre-treatment result minus the post-treatment result divided by the pre-treatment result. As is apparent from this analysis, values nearest to 1.00 indicate stronger relative tensile properties.

TABLE III

| Example | Composition of Mixture (Relative Parts) | pH | Degree of Curl Dry | After 48 Hrs @ 90% Humidity | Instron Force (S) |
|---|---|---|---|---|---|
| 1 | Part A:Part D | 9.2 | 1.00 | 1.07 | 1.00 |
| 2 | Part A:Part B | 4.0 | 1.40 | 1.53 | 1.03 |
| 3 | Part A:Part B: 0.01 Part E | 4.7 | 0.98 | 1.03 | 1.05 |
| 4 | Part A:Part B: 0.01 Part F | 4.7 | 1.00 | 1.03 | 1.07 |
| 5 | Part A:Part B: 0.005 Part G | 3.2 | 0.98 | 1.03 | 1.04 |
| 6 | Part A:Part B: 0.01 Part H | 3.7 | 0.96 | 0.99 | — |
| 7 | Part B:Part C: 0.01 Part E | 4.8 | 1.60 | — | — |
| 8 | Part B:Part C: 0.01 Part F | 3.2 | 1.73 | — | — |
| 9 | Part B:Part C: | 3.6 | 1.73 | — | — |
| | 0.005 Part G | | | | |
| 10 | Part A:Part B: 0.000001 CI Basic Violet 10** | 4.0 | 1.40 | 1.50 | — |
| 11 | Part A:Part B: 0.001 Basic Violet then, 20 vol. peroxide:CI Acid Violet 43** | 3.2 | 1.33 | 1.56 | — |
| 12 | Part A:Part B: 0.5% Merquat S* | 4.4 | 1.13 | 1.37 | — |
| 13 | Part A:Part B: 1.0% Merquat S* | 4.4 | 1.43 | 1.41 | — |

*Merquat S is the trade name for a quarternary amine component produced by Merck, Inc.
**Colour Index number of dyestuff A review of the test results provided in Table III clearly demonstrates that the inclusion of a fluoroscein-based dye in the permanent wave composition substantially improves the curl retention characteristics of the resulting permanent waved hair, as well as improving the structural integrity of the hair over hair reduced at an alkaline pH. In particular, where Xanthene and anthraquinone dyes were employed in the relaxing solution, the structural integrity of the resulting hair was not enhanced, as was provided by the fluoroscein-based dye stuffs.

In Table IV, examples of the range of colors attainable by employing the present invention are provided, along with the resistance to color change attained by the composition of this invention after repeated shampooing or exposure to sunlight. Table IV clearly shows the increased durability of the dye when incorporated into the relaxing solution of the present invention as opposed to prior art conventional methods.

In Table IV, the hair samples were prepared and permanent waved as detailed above in reference to Table III. The information provided in Table IV represents the chromicity values, L, A, and B for the same hair sample before and after seven shampoo, rinse and dry cycles, as well as after exposure to ten hours of simulated sunlight. Except where noted, medium brown hair was used. All of the measurements were taken employing a Spectrogard II system available from Pacific Instruments.

TABLE IV

| Example | Composition of Mixture (Relative Parts) | Color | Chromicity Values: L, A, B Initial | After Shampooing | After 10 Hrs Shampooing |
|---|---|---|---|---|---|
| 14 | Part A:Part B: 0.01 Part F | Light Auburn | L = 21.84 a = 11.66 b = 10.07 | L = 21.45 a = 11.62 b = 10.39 | L = 20.36 a = 14.28 b = 9.31 |
| 15 | Part A:Part B: 0.01 Part E | Auburn | L = 21.25 a = 12.08 b = 9.65 | L = 20.99 a = 11.49 b = 9.43 | L = 21.48 a = 12.69 b = 9.49 |
| 16 | Part A:Part B: 0.01 Part G | Dark Auburn | L = 21.18 a = 9.11 b = 6.71 | L = 20.64 a = 9.68 b = 7.93 | L = 22.28 a = 8.70 b = 8.59 |
| 17 | Part A:Part B: 0.01 Part D | Blue/ Brown | L = 15.33 a = 2.15 b = 3.31 | L = 15.75 a = 2.21 b = 3.29 | L = 16.28 a = 2.38 b = 3.23 |
| 18 | Part A:Part B: 0.01 part D on blended grey hair | Blue/ Grey | L = 39.90 a = −2.00 b = 0.32 | L = 41.55 a = −3.24 b = 0.31 | L = 43.15 a = −3.65 b = 0.30 |
| 19 | Part A:Part B: 0.01 Part F on White Hair | Pink | L = 41.70 a = 49.44 b = 27.44 | L = 41.27 a = 49.25 b = 27.05 | L = 41.65 a = 49.33 b = 26.93 |
| 20 | Part B: 0.01 on White Hair | Light Pink | L = 55.00 a = 20.76 b = 3.14 | L = 78.26 a = 8.72 b = 6.55 | L = 56.92 a = 13.70 b = 5.36 |

Chromicity values of L = total reflectance of 0 = black, 100 = white; a = (+) for red; (−) for green; b = (+) yellow, (−) for blue as determined by the average of triplicate measurements performed on a Spectrogard II system available from Pacific Instruments.

It will thus be seen that the objects set forth above, among those made apparent from the preceding description are efficiently attained and, since certain changes may be made in the composition detailed herein, as well as in carrying out the above process without departing from the scope of the invention, it is intended that all matter contained in the above description shall be interpreted as illustrative and not in a limiting sense.

It is to be understood that the following claims are intended to coverall of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A process for permanently waving hair while simultaneously coloring the hair comprising the steps of:

A. preparing the hair for the application of a permanent wave solution in the conventional manner;

B. mixing the hair coloring and permanent waving solution just prior to its application to the hair by combining a fluoroscein-based dye with a permanent waving solution comprising one selected from the group consisting of an ester of thioglycolic acid, an ester of thiolactic acid, and an amide of 2-aminothiol;

C. adjusting the pH of the composition to be between about 2.5 and 4.5;

D. applying the hair dyeing and coloring composition to the hair in the conventional manner; and E. completing the permanent waving process in a conventional manner.

2. The method defined in claim 1, comprising the additional steps of

F. applying the permanent waving and hair dyeing solution to the hair after wrapping the hair about a styling rod, G. allowing the solution to remain on the hair for between about 5 and 60 minutes, and H. rinsing the permanent waving and hair dyeing solution from the hair with water.

3. The method defined in claim 2, comprising the additional steps of:

(I) applying a solution of between about 0.2% and 6% hydrogen peroxide to the hair after removal of the permanent waving and coloring solution; and (J) allowing the hydrogen peroxide to remain on the hair for between about 5 and 30 minutes.

4. The method defined in claim 3, comprising the additional step of:

(I) applying a solution of between about 0.02% and 16% of a peroxohalogen salt to the hair after removal of the permanent wave and coloring composition; and (J) allowing the peroxohalogen salt to remain on the hair for between about 5 and 30 minutes.

5. The method defined in claim 4, wherein the peroxohalogen salt is further defined as comprising at least one selected from the group consisting of a metal salt, an ammonium salt, and a phosphonium salt formed from one selected from the group consisting of bromate, borate, chlorate, chlorite and persulfate.

* * * * *